United States Patent
Hawley et al.

(10) Patent No.: US 7,005,449 B2
(45) Date of Patent: Feb. 28, 2006

(54) TOLTERODINE SALTS

(75) Inventors: Michael Hawley, Kalamazoo, MI (US); Satish Kumar Singh, Portage, MI (US); Walter Morozowich, Kalamazoo, MI (US); Mark P. Warchol, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 273 days.

(21) Appl. No.: 10/127,875

(22) Filed: Apr. 23, 2002

(65) Prior Publication Data

US 2003/0199582 A1 Oct. 23, 2003

(51) Int. Cl.
A61K 31/205 (2006.01)
C07C 215/56 (2006.01)
C07C 209/00 (2006.01)

(52) U.S. Cl. .............. 514/555; 562/490; 564/395; 564/413

(58) Field of Classification Search ........... 514/555; 562/490; 564/395, 413; 549/399
See application file for complete search history.

(56) References Cited

U.S. PATENT DOCUMENTS 5,382,600 A 1/1995 Jönsson et al.
5,559,269 A 9/1996 Johansson et al.
5,922,914 A * 7/1999 Gage et al. ............ 564/413

FOREIGN PATENT DOCUMENTS

WO   WO9829402   7/1998
WO   WO0234245   5/2002

OTHER PUBLICATIONS

Postlind et al, *Drug Metabolism and Disposition*, 26(4):289–293.
Mooney et al, *Journal of Pharmaceutical Sciences*, 70(1):13–22 (1981).
Nilvebrant et al, *Pharmacology & Toxicology*, 81:169–172 (1997).

* cited by examiner

*Primary Examiner*—Cecilia J. Taang
*Assistant Examiner*—Taylor V. Oh
(74) *Attorney, Agent, or Firm*—Dinsmore & Shohl LLP

(57) ABSTRACT

The present invention concerns novel pharmaceutically active compounds, pharmaceutical compositions containing the same, the compounds for use as medicaments, and use of the compounds for the manufacture of specific medicaments. The present invention also concerns a method of treatment involving administration of the compounds.

Specifically, the compounds are pharmaceutically acceptable salts of tolterodine or hydroxytolterodine, wherein the salt is of an acid selected from the group consisting of aliphatic mono- and dicarboxylic acids comprising from 7 to 24 carbon atoms, alkanedisulfonic acids comprising from 2 to 4 carbon atoms, naphthoic acid derivatives comprising from 11 to 27 carbon atoms, maleic acid and fumaric acid.

29 Claims, 1 Drawing Sheet

TOLTERODINE SALTS

TECHNICAL FIELD

The present invention concerns novel pharmaceutically active compounds, pharmaceutical compositions containing the same, the compounds for use as medicaments, and use of the compounds for the manufacture of specific medicaments. The present invention also concerns a method of treatment involving administration of the compounds. Specifically, the compounds are certain salts of tolterodine or hydroxytolterodine.

The novel compounds are useful as antimuscarinic agents. In particular, the novel compounds are useful for the treatment of asthma, a group of breathing disorders termed Chronic Obstructive Pulmonary Disease (COPD), asthma, allergic rhinitis, and urinary disorder.

More specifically, said compounds are advantageously administered by inhalation or insufflation.

BACKGROUND OF THE INVENTION

U.S. Pat. No. 5,382,600 discloses (substituted) 3,3-diphenylpropylamines useful for treating urinary incontinence. In particular, it discloses 2-[(1R)-3-(diisopropylamino)-1-phenylpropyl)-4-methylphenol, also known as N,N-diisopropyl-3-(2-hydroxy-5-methylphenyl)-3-phenylpropylamine, with the generic name of tolterodine, as being useful to treat urinary incontinence. Tolterodine is the compound of Example 22 of U.S. Pat. No. 5,382,600.

It is preferred that tolterodine is prepared by the processes of International Publication WO98/29402.

H Postlind et al, Drug Metabolism and Disposition, 26(4): 289–293 (1998) discloses that tolterodine is a muscarinic receptor antagonist. It is presently being sold in a number of different countries for treatment of urinary incontinence under the name Detrol®, marketed by Pharmacia. When tolterodine is used to treat urinary incontinence it is administered perorally as a tablet. The major, active metabolite of tolterodine is the 5-hydroxymethyl derivative of tolterodine.

U.S. Pat. No. 5,559,269 and H Postlind et al, Drug Metabolism and Disposition, 26(4): 289–293 (1998) disclose hydroxytolterodine. U.S. Pat. No. 5,559,269 discloses this compound as being useful to treat urinary incontinence. Pharmacol. Toxicol., 81: 169–172 (1997) discloses that hydroxytolterodine has antimuscarinic activity.

WO98/29402 mentions tolterodine salts of the following acids: methanesulfonic, hydrochloric, hydrobromic, sulfuric, phosphoric, nitric, benzoic, citric, tartaric, fumaric, maleic, $CH_3—(CH_2)_n—COOH$ where n is 0 thru 4, and $HOOC—(CH_2)_n—COOH$ where n is as defined above.

PCT/US01/27779 discloses the use of tolterodine for treating asthma, COPD, and allergic rhinitis.

The currently marketed administration form of tolterodine is film-coated tablets containing 1 mg, 2 mg or 4 mg of tolterodine L-tartrate for release in the gastrointestinal tract. Consumers constantly require alternative delivery forms with favorable efficacy and/or which simplify the treatment, thus improving their quality of life.

Despite the above advances in the art, it is desirable to develop novel pharmaceutical compounds that further improve the quality of life for a large number of individuals.

SUMMARY OF THE INVENTION

For these and other purposes, it is an object of the present invention to provide highly efficient pharmaceutical compounds for treatment of asthma.

It is also an object of the present invention to provide highly efficient pharmaceutical compounds for treatment of COPD.

It is a further object of the present invention to provide highly efficient pharmaceutical compounds for treatment of allergic rhinitis.

It is an object of the present invention to provide highly efficient pharmaceutical compounds for treatment of urinary disorder.

It is also an object of the present invention to provide highly efficient, inhalable or insufflable antimuscarinic compounds.

It is also an object of the present invention to provide a pharmaceutical composition, comprising an antimuscarinic compound, which is appropriate for alternative delivery forms.

Another object of the present invention is to provide a novel use of an antimuscarinic compound for the manufacture of a medicament for therapeutical treatment of asthma, COPD, allergic rhinitis, and urinary disorder.

Finally, it is an object of the present invention to decrease undesirable systemic exposure upon treatment of a medical condition with an antimuscarinic agent.

For these and other objects that will be evident from the following disclosure, the present invention provides a pharmaceutically acceptable salt of tolterodine or hydroxytolterodine, wherein the salt is of an acid selected from the group consisting of aliphatic mono- and dicarboxylic acids comprising from 7 to 24 carbon atoms, alkanedisulfonic acids comprising from 2 to 4 carbon atoms, and naphthoic acid derivatives comprising from 11 to 27 carbon atoms.

In an embodiment of the pharmaceutically acceptable salt of tolterodine or hydroxytolterodine according to the invention, said acid is selected from the group consisting of: $CH_3—(CH_2)_{n1}—COOH$, wherein n1 is an integer in the range of 5–16, $HOOC—(CH_2)_{n2}—COOH$, wherein n2 is an integer in the range of 5–16, and $HO_3S—(CH_2)_{n3}—SO_3H$, wherein n3 is an integer in the range of 2–4.

In another embodiment of the pharmaceutically acceptable salt of tolterodine or hydroxytolterodine according to the invention, said acid is selected from the group consisting of: $CH_3—(CH_2)_{n1}—COOH$, wherein n1 is an integer in the range of 5–16, and $HOOC—(CH_2)_{n2}—COOH$, wherein n2 is an integer in the range of 5–16. In a preferred embodiment, n1 is an integer in the range of 8–12, and n2 is an integer in the range of 8–12.

In yet another embodiment of the pharmaceutically acceptable salt of tolterodine or hydroxytolterodine according to the invention, said acid is selected from the group consisting of naphthoic acid derivatives comprising from 11 to 27 carbon atoms of the formula:

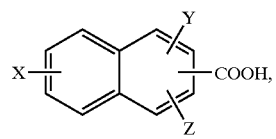

wherein X and Y are independently selected from the group consisting of —H, —OH, —CH$_3$, —F, —Cl, —Br, —I, —COOH, —NO$_2$, —SO$_3$H, and —CF$_3$, and Z is selected from the group consisting of —H and

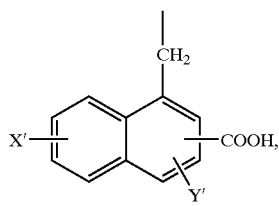

wherein X' and Y' are independently selected from the group consisting of —H, —OH, —CH$_3$, —F, —Cl, —Br, —I, —COOH, —NO$_2$, —SO$_3$H, and —CF$_3$. It is preferred that X, Y, X', and Y' are independently selected from the group consisting of —H, —OH, and —COOH. It is particularly preferred that X and X' are —H, and Y and Y' are —OH.

In one preferred embodiment of the pharmaceutically acceptable salt of tolterodine or hydroxytolterodine according to the invention, said acid is selected from the group consisting of heptanoic acid, capric acid, lauric acid, pamoic acid, 1-hydroxy-2-naphthoic acid, 2-hydroxy-1-naphthoic acid, and 1,2-ethanedisulfonic acid.

In a preferred embodiment, said pharmaceutically acceptable salt of tolterodine or hydroxytolterodine according to the invention is in its crystal form.

The present invention also provides a pharmaceutical composition comprising a therapeutically effective amount of a salt according to the invention, and a suitable pharmaceutical diluent or carrier therefor. In a preferred embodiment, said composition is inhalable or insufflable.

The present invention provides a salt according to the invention for use as a medicament.

The present invention also provides a novel use of a pharmaceutically acceptable salt of tolterodine or hydroxytolterodine, wherein the salt is of an acid selected from the group consisting of aliphatic mono- and dicarboxylic acids comprising from 7 to 24 carbon atoms, alkanedisulfonic acids comprising from 2 to 4 carbon atoms, naphthoic acid derivatives comprising from 11 to 27 carbon atoms, maleic acid and fumaric acid, for the manufacture of a medicament for treating a disorder selected from the group consisting of asthma, chronic obstructive pulmonary disease (COPD), allergic rhinitis, and urinary disorder. In a preferred embodiment, said medicament is inhalable or insufflable.

The present invention additionally provides a method of treating a disorder in a mammal, including man, comprising administering to said mammal, in need of such a treatment, a therapeutically effective amount of a salt or a composition according to the invention. In a preferred embodiment, said administration is performed by inhalation or insufflation.

The present invention also provides a method of treating a disorder selected from the group consisting of asthma, chronic obstructive pulmonary disease (COPD), allergic rhinitis, and urinary disorder, in a mammal, including man, comprising administering to said mammal, in need of such a treatment, a therapeutically effective amount of a pharmaceutically acceptable salt of tolterodine or hydroxytolterodine, wherein the salt is of an acid selected from the group consisting of aliphatic mono- and dicarboxylic acids comprising from 7 to 24 carbon atoms, alkanedisulfonic acids comprising from 2 to 4 carbon atoms, naphthoic acid derivatives comprising from 11 to 27 carbon atoms, maleic acid and fumaric acid. The above-mentioned salts are also useful in a method of treating a disorder selected from the group consisting of asthma, chronic obstructive pulmonary disease (COPD), allergic rhinitis, and urinary disorder, in a mammal, including man, comprising administering to said mammal, in need of such a treatment, a therapeutically effective amount of a pharmaceutical composition comprising a therapeutically effective amount of a salt according to the invention, and a suitable pharmaceutical diluent or carrier therefor. In a preferred embodiment, said administration is performed by inhalation or insufflation.

Finally, the present invention provides a device containing an inhalable or insufflable pharmaceutical composition according to the invention.

DESCRIPTION OF THE INVENTION

Figure 1:
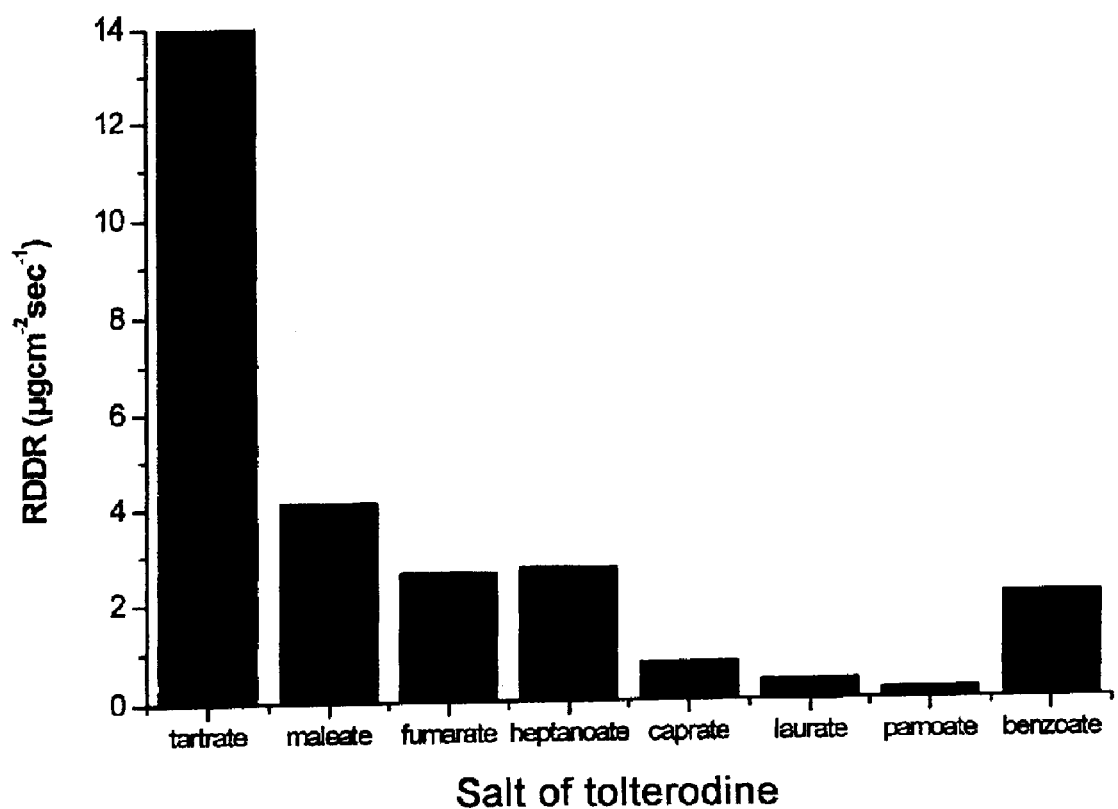
FIG. 1: Rotating disk dissolution data for various salts of tolterodine at 25° C., pH 6, 0.05 M phosphate.

In describing the preferred embodiments, certain terminology will be utilized for the sake of clarity. Such terminology is intended to encompass the recited embodiments, as well as all technical equivalents that operate in a similar manner for a similar purpose to achieve a similar result. To the extent that any pharmaceutically active compound is disclosed or claimed, it is expressly intended to include all active metabolites produced in vivo, and, is expressly intended to include all enantiomers, isomers or tautomers where the compound is capable of being present in its enantiomeric, isomeric or tautomeric form.

The compounds of the invention can be prepared by one skilled in the art just by knowing the chemical structure of the compound to be prepared. The invention is the compounds themselves, not the process chemistry to make them. The chemistry is known to those skilled in the art.

The compounds, compositions, and methods of the present invention are useful to treat mammals, including man. It is preferred that the mammal is a human.

The present invention involves the use of antimuscarinic compounds for therapeutical treatment of certain medical conditions, such as asthma, COPD, allergic rhinitis, and urinary disorder.

The compounds of the present invention are salts of tolterodine and derivatives thereof, specifically including salts of hydroxytolterodine. What is said in the following for tolterodine is also meant to include any active derivatives thereof, particularly hydroxytolterodine.

Upon traditional tablet administration of tolterodine, the plasma concentration thereof increases, peaking after 1–2 hours. Tolterodine is mainly metabolized by the liver following oral dosing. According to the present invention, administration of certain salts of tolterodine to patients in need thereof can advantageously be performed via inhalation or insufflation. Thereby, tolterodine elicits local effects, and the systemic effects are lessened or delayed, since the compounds according to the invention do not readily gain access to the systemic circulation.

The compositions according to the invention can be made up in solid or liquid form, such as powders, crystals, sterile solutions, suspensions or emulsions, and the like.

The compounds of the present invention are administered by inhalation or insufflation. The inhalation or insufflation is preferably by either an aerosol or a powder.

The methods, the compounds and compositions of the present invention are useful for the treatment of acetylcholine-mediated disorders. In particular, they are useful for treating asthma, COPD, allergic rhinitis, and urinary disorder.

"Asthma" refers to a chronic lung disease causing bronchoconstriction (narrowing of the airways) due to inflammation (swelling) and tightening of the muscles around the airways. The inflammation also causes an increase in mucus production, which causes coughing that may continue for extended periods. Asthma is characterized by recurrent episodes of breathlessness, wheezing, coughing, and chest tightness, termed exacerbations. The severity of exacerbations can range from mild to life threatening. The exacerbations can be a result of exposure to e.g. respiratory infections, dust, mold, pollen, cold air, exercise, stress, tobacco smoke, and air pollutants.

"COPD" refers to Chronic Obstructive Pulmonary Disease, primarily associated with past and present cigarette smoking. It involves airflow obstruction, mainly associated with emphysema and chronic bronchitis. Emphysema causes irreversible lung damage by weakening and breaking the air sacs within the lungs. Chronic Bronchitis is an inflammatory disease, which increases mucus in the airways and bacterial infections in the bronchial tubes,resulting in obstructed airflow.

"Allergic rhinitis" refers to acute rhinitis or nasal rhinitis, including hay fever. It is caused by allergens such as pollen or dust. It may produce sneezing, congestion, runny nose, and itchiness in the nose, throat, eyes, and ears.

"Urinary disorders" and symptoms thereof include some or all of the following: urgency, frequency, incontinence, urine leakage, enuresis, dysuria, hesitancy, and difficulty of emptying bladder. In particular, urinary disorders include urinary incontinence, caused by e.g. unstable or overactive urinary bladder.

Overactive urinary bladder encompasses variants of urinary disorders, including overactive detrusor (detrusor instability, detrusor hyperreflexia) and sensory urgency, as well as symptoms of detrusor overactivity, e.g. urge incontinence, urgency, urinary frequency, and LUTS (Lower Urinary Tract Symptoms), including obstructive urinary symptoms, such as slow urination, dribbling at the end of urination, inability to urinate and/or the need to strain to urinate at an acceptable rate, or irritating symptoms such as frequency and/or urgency).

Other conditions are also included, which give rise to urinary frequency, urgency and/or urge incontinence. Overactive bladder disorders also include nocturia and mixed incontinence. While overactive bladder is often associated with detrusor muscle instability, disorders of bladder function may also be due to neuropathy of the central nervous system (detrusor hyperreflexia), including spinal cord and brain lesions, such as multiple sclerosis and stroke. Overactive bladder symptoms may also result from, for example, male bladder outlet obstruction (usually due to prostatic hypertrophy), interstitial cystitis, local edema and irritation due to focal bladder cancer, radiation cystitis due to radiotherapy to the pelvis, and cystitis.

A specific problem which can be treated by the claimed method is a dry overactive bladder, which includes frequency, urgency and nocturia.

The dosage of the specific compound will vary depending on its potency, the mode of administration, the age and weight of the patient and the severity of the condition to be treated. The daily dosage may, for example, range from about 0.01 mg to about 4 mg per kg of body weight, administered singly or multiply in doses e.g. from about 0.05 mg to about 200 mg each. A clinically effective amount of a compound according to the invention is from about 0.05 mg to about 12 mg. It is preferred that the effective amount is from about 0.1 to about 6 mg; it is more preferred that the effective amount is from about 0.2 to about 5 mg.

The dosage form for inhalation can be an aerosol. The minimum amount of an aerosol delivery is about 0.2 ml and the maximum aerosol delivery is about 5 ml. The concentration of the compound according to the invention may vary as long as the total amount of spray delivered is within the about 0.2 to about 5 ml amount and it delivers an effective amount. It is well known to those skilled in the art that if the concentration is higher, one gives a smaller dose to deliver the same effective amount.

The non-active ingredient or carrier can be just (sterile) water with the pH adjusted to where the active pharmaceutical compound is soluble. It is preferred that the pH is at or near 7. Alternatively and preferably, the non-active carrier agent should be physiological saline with the pH adjusted appropriately. Aerosols for inhalation of various pharmaceutical agents are well known to those skilled in the art, including many aerosols for treating asthma.

Alternatively, the dosage form for inhalation can be a powder. Powders for inhalation of various pharmaceutical agents are well known to those skilled in the art, including many powders for treating asthma. When the dosage form is a powder, the compound according to the invention can be administered in pure form, e.g. pure crystal form, or diluted with an inert carrier. When an inert carrier is used, the compound according to the invention is compounded such that the total amount of powder delivered delivers an "effective amount" of the compound. The actual concentration of the compound may vary. If the concentration is lower, then more powder must be delivered; if the concentration is higher, less total material must be delivered to provide an effective amount of the compound.

Various devices are on the market for administering powders for inhalation for asthma, and these devices are suitable for administering the compounds and compositions of the present invention.

The carriers may be of any inert material, organic or inorganic, suitable for administration via inhalation or insufflation, such as: water, gelatin, gum arabicum, lactose, microcrystalline cellulose, starch, sodium starch glycolate, calcium hydrogen phosphate, magnesium stearate, talcum, colloidal silicon dioxide, and the like.

The compositions according to the invention may also contain other pharmaceutically active agents, and conventional additives, such as stabilizers, wetting agents, emulsifiers, flavoring agents, buffers, and the like.

Pharmaceutically acceptable salts according to the present invention include salts of the following acids: aliphatic mono- and dicarboxylic acids comprising from 7 to 24 carbon atoms, alkanedisulfonic acids comprising from 2 to 4 carbon atoms, naphthoic acid derivatives comprising from 11 to 27 carbon atoms, maleic acid and fumaric acid.

A preferred salt is of naphthoic acid or derivatives thereof. Naphthoic acid refers to naphthalene-1-carboxylic acid and naphtalene-2-carboxylic acid. Naphthoic acid derivatives comprise naphthoic acid substituted with at least one of the following: hydrogen, methyl, halogen (fluorine, chlorine, bromine, iodine), carboxyl, nitro, sulfo and trifluoromethyl, preferably with hydrogen, hydroxyl, or carboxyl. Both of the naphthoic acid aromatic rings may be independently substituted.

Naphthoic acid derivatives also comprise naphthoic acid substituted with another naphthoic acid (derivative), optionally via a linker. For example, a naphthoic acid (derivative) may be substituted with an alkylnaphthoic acid (derivative). Both of the rings of each of the two naphthoic acid structures may be independently substituted with at least one of the following: hydrogen, methyl, halogen (fluorine, chlorine, bromine, iodine), carboxyl, nitro, sulfo and trifluoromethyl, preferably with hydrogen, hydroxyl, or carboxyl.

It is preferred that the naphthoic acid derivative comprises from 11 to 27 carbon atoms.

Particularly preferred salts include salts of pamoic acid, 1-hydroxy-2-naphthoic acid, and 2-hydroxy-1-naphthoic acid. Pamoic acid, or embonic acid, is 4,4'-methylenebis (3-hydroxy-2-naphthoic acid).

Other preferred salts include salts of aliphatic mono- or dicarboxylic acids containing more than 6 carbon atoms and less than 25 carbon atoms, i.e. aliphatic mono- or dicarboxylic acids comprising from 7 to 24 carbon atoms. The acids may be saturated or partially unsaturated, as long as their corresponding bases are soluble in aqueous solution to any extent.

Particularly preferred salts are of aliphatic mono- or dicarboxylic acids comprising from 7 to 18 carbon atoms, even more preferred from 10 to 14. Preferred mono- or dicarboxylic acid salts are of unbranched mono- or dicarboxylic acids, more preferred unbranched monocarboxylic acids.

Particularly preferred salts are of heptanoic acid (7 C), capric acid (10 C), and lauric acid (12 C).

Other preferred salts are of maleic acid and fumaric acid.

Other preferred salts are of alkanedisulfonic acids containing at least 2 carbon atoms but less than 5 carbon atoms, i.e. alkanedisulfonic acids comprising from 2 to 4 carbon atoms. A preferred specific salt is of 1,2-ethanedisulfonic acid (edisylate).

The salts according to the invention have been found to dissolve rather slowly in aqueous solution, resulting in a long duration of action. This property makes them highly appropriate for pulmonary delivery of tolterodine and hydroxytolterodine, since they inventively provide local effects in the lungs upon inhalation, which is particularly useful for the treatment of respiratory tract disorders, such as asthma, COPD and allergic rhinitis.

Thus, the salts according to the invention spread the absorption of the drug out over a longer period of time. This is advantageous for the treatment of asthma, COPD and allergic rhinitis, since it is cost-effective and reduces the risk of side effects associated with systemic exposure in the subject.

However, systemic distribution still occurs at a modest rate. Therefore, the salts according to the invention are also useful for the treatment of urinary disorder when a slow release is desirable. This may for example be the case when a prolonged effect is of interest, and may contribute to preventing or diminishing of side effects from the therapeutical treatment. If desirable, systemic distribution may also be achieved through e.g. oral administration.

Advantageously, the composition according to the invention is contained in a suitable device for delivery to the subject. Examples of such devices include aerosol containers and devices for powder administration.

Specifically, the compositions according to the present invention have proved to be very suitable for administering the above-mentioned drug tolterodine and would likewise be suitable for its related compounds, i.e. the major, active metabolite of tolterodine, i.e. (R)-N,N-diisopropyl-3-(2-hydroxy-5-hydroxymethylphenyl)-3-phenylpropanamine; the corresponding (S)-enantiomer to tolterodine, i.e. (S)-N,N-diisopropyl-3-(2-hydroxy-5-methylphenyl)-3-phenylpropanamine; the 5-hydroxymethyl metabolite of the (S)-enantiomer, i.e. (S)-N,N-diisopropyl-3-(2-hydroxy-5-hydroxymethylphenyl)-3-phenylpropanamine; as well as the corresponding racemate to tolterodine, i.e. (R,S)-N,N-diisopropyl-3-(2-hydroxy-5-methylphenyl)-3-phenylpropanamine; and prodrug forms and pharmacologically acceptable salts thereof.

Tolterodine refers to 2-[(1R)-3-(diisopropylamino)-1-phenylpropyl]-4-methylphenol, also known as (R)-N,N-diisopropyl-3-(2-hydroxy-5-methylphenyl)-3-phenylpropylamine, a compound of the formula:

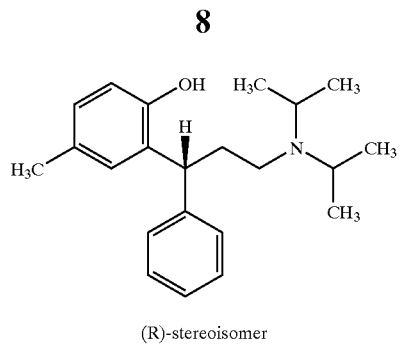

(R)-stereoisomer

Hydroxytolterodine refers to 2-[(1R)-3-(diisopropylamino)-1-phenylpropyl]-4-(hyrdroxymethyl) phenol, a compound of the formula:

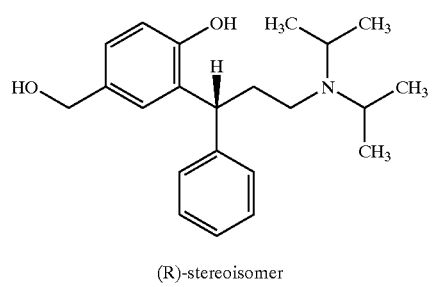

(R)-stereoisomer

"Antimuscarinic agents" refer to muscarinic receptor antagonists. Examples of antimuscarinic agents include, but are not limited to, tolterodine, hydroxytolterodine, 2-(diisopropylamino)ethyl-1-phenylcyclopentanecarboxylate, propiverine, oxybutynin, trospium, darifenacin, temiverine, and ipratropium.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Analogously, "inhalably acceptable" and "insufflably acceptable", respectively, refer to properties and/or substances which are pharmaceutically acceptable and also suitable for use via inhalation and insufflation, respectively.

EXAMPLES

Without further elaboration, it is believed that one skilled in the art can, using the preceding description, practice the present invention to its fullest extent. The following detailed examples are to be construed as merely illustrative, and not as limitations of the preceding disclosure in any way.

Example 1

Crystallization and Dissolution Rates of Several Salts of Tolterodine

Tolterodine tartrate was used as the source of tolterodine for all experiments. A small amount of tolterodine free base in toluene (~1 gram) was prepared by neutralizing the tartrate salt with sodium carbonate and sodium hydroxide and then extracting it into toluene.

Several salts of tolterodine were prepared. The benzoate, caprate, fumarate, heptanoate, laurate, maleate and pamoate salts were all crystallized. The procedure involved the addition of an approximately equimolar amount of the counterion of choice to either tolterodine free base or tolterodine tartrate. Crystallization was achieved using standard techniques, known to a person skilled in the art.

Data was collected on the salts. Rotating disk dissolution data was collected at pH 6 in a 0.05 M phosphate buffer at 25° C. on a fiber optic apparatus.

Table 1 shows a summary of the results for the eight salts that were crystallized. Powder X-ray data and optical microscopy were used to confirm that the salts were indeed crystalline and distinct. The DSC (Differential Scanning Calorimetry) data showed that the melting points of the salts varied widely, from about 60° C. for the caprate and laurate salts up to 260° C. for the fumarate salt.

TABLE 1

| Tolterodine salt | Melting point (° C.) | Heat of fusion (J/g) | Rotating disk dissolution rate (RDDR; $\mu g\ cm^{-2} s^{-1}$) |
|---|---|---|---|
| tartrate | 216 | 127 | 14.0 |
| benzoate | 167–173 | pc | 2.1 |
| caprate | 62 | 74 | 0.75 |
| fumarate | 259 | dc | 2.6 |
| heptanoate | 97 | 78 | 2.7 |
| laurate | 59–70 | 61 | 0.38 |
| maleate | 177 | 119 | 4.1 |
| pamoate | 127 | 25 | <0.3 | pc = phase conversion
dc = decomposition

The physical property of most interest in this study is the dissolution rate. These data are shown graphically in FIG. 1. The salts according to the invention show a variation in dissolution rates of greater than an order of magnitude. Furthermore, all of the salts dissolve at a rate slower than that of the reference material, tolterodine tartrate.

FIG. 1 shows that the series of carboxylic acid salts, heptanoic, capric and lauric produced sequentially lower dissolution rates as the number of carbons was increased from seven to ten to twelve. This suggests that the dissolution rate for salts of other long chain carboxylic acids with tolterodine may have dissolution rates proportional to the number of carbon atoms in the chain. For example, palmitic (16 C) and myristic (14 C) acid salts of tolterodine would have very low predicted dissolution rates. The dissolution rate for the pamoate salt could not be measured, because the value was less than the detection limit of the instrument.

According to the Mooney Model (Mooney K G, Minutn M A, Himmelstein, K J, Stella V J, "Dissolution kinetics of carboxylic acids I: Effect of pH under unbuffered conditions" Journal of Pharm Sciences, 70, 13–22, 1981), the measured dissolution rates and the solubility of tolterodine tartrate can be used to estimate the solubility of the remaining salts. This calculation produces solubility values from about three to 0.3 mg/mL (in free base equivalents) for the examined salts.

Thus, seven different salts of tolterodine have been isolated. The dissolution rates of the salts vary over greater than one order of magnitude. Similar differences in dissolution rates for the salts of more the highly active metabolite, hydroxytolterodine, are expected.

In summary, seven different salts of tolterodine have been crystallized. For the seven salts that were crystallized, we have measured a range of rotating disk dissolution rates from 4.1 to <0.3 $\mu g\ cm^{-2} sec^{-1}$ at 25° C. in pH 6 media. These salts dissolve slower than tolterodine tartrate, which has a rotating disk dissolution rate of 14 $\mu g\ cm^{-2} sec^{-1}$ under these conditions.

It is possible that salts of pamoic acid may produce a salt whose bioavailability can be limited by dissolution.

Example 2

Equilibrium Solubility of Several Salts of Tolterodine

Different tolterodine salts (HCl, mesylate, tartrate, edisylate and maleate) were prepared in a similar manner to that described in Example 1. Solubility of different tolterodine salts were determined by shaking an excess of salt in the solvent(water and 0.1 M phosphate buffer pH 7.4, respectively) for 24 hours at room temperature. The resultant solution is centrifuged at 5000 rpm for 30 min in a temperature-controlled centrifuge. The supernatant was diluted and analysed for tolterodine by reversed phase high performance liquid chromatography (RP-HPLC). The results are shown in Table 2.

TABLE 2

| | Equilibrium solubility [mg/ml] | |
|---|---|---|
| Tolterodine salt | in water (final pH) | in buffer (final pH) |
| HCl | 8.7 (7.0) | 7.5 (7.3) |
| Mesylate | 170 (1.7) | 175 (1.2) |
| Tartrate | 11.4 (3.6) | 9.8 (4.4) |
| Edisylate | 7.1 (3.7) | 8.4 (7.3) |
| Maleate | 1.5 (5.0) | 4.7 (6.9) |

Example 3

Administration of Tolterodine and Hydroxytolterodine Salts

Example 3A

A 50 years old male with a history of chronic COPD with $FEV_1$ of 1.4 l is treated with inhalation of tolterodine pamoate powder 1 mg every 8 hr continuously for dyspnea.

Example 3B

A 55 year old female with a with a history of chronic COPD with a history of chronic COPD with $FEV_1$ of 1.5 l is treated with inhalation of hydroxytolterodine caprate 2 mg every 12 hr continuously for dyspnea.

Example 3C

A 30 year old female with a history of asthma with a morning peak flow of less than 2.1 l/sec is treated with inhalation of tolterodine heptanoate 0.5 mg every 8 hr continuously.

Example 3D

A 25 year old male with a history of asthma with a morning peak flow of 4 l/sec is treated with inhalation of hydroxytolterodine laurate powder 5 mg once a day continuously.

Example 3E

A 50 year old female with a history of severe asthma with a morning peak flow of less than 3 l/sec is treated with inhalation of tolterodine edisylate powder 3 mg twice a day continuously.

What is claimed is:

1. A pharmaceutically acceptable salt of tolterodine or hydroxytolterodine, wherein the salt is of an acid selected from the group consisting of aliphatic mono- and dicarboxylic acids of from 7 to 24 carbon atoms, alkanedisulfonic acids of from 2 to 4 carbon atoms, and naphthoic acid derivatives of from 11 to 27 carbon atoms.

2. A pharmaceutically acceptable salt of tolterodine or hydroxytolterodine according to claim 1, wherein said acid is selected from the group consisting of: $CH_3$—$(CH_2)_{n1}$—COOH, wherein n1 is an integer in the range of 5–16, HOOC—$(CH_2)_{n2}$—COOH, wherein $n_2$ is an integer in the range of 5–16, and $HO_3S$—$(CH_2)_{n3}$—$SO_3H$, wherein $n_3$ is an integer in the range of 2–4.

3. A pharmaceutically acceptable salt of tolterodine or hydroxytolterodine according to claim 2, wherein said acid is selected from the group consisting of: $CH_3$—$(CH_2)_{n1}$—COOH, wherein n1 is an integer in the range of 5–16, and HOOC—$(CH_2)_{n2}$—COOH, wherein n2 is an integer in the range of 5–16.

4. A pharmaceutically acceptable salt of tolterodine or hydroxytolterodine according to claim 1, wherein said acid is selected from the group consisting of heptanoic acid, capric acid, lauric acid, pamoic acid, 1-hydroxy-2-naphthoic acid, 2-hydroxy-1-naphthoic acid, and 1,2-ethanedisulfonic acid.

5. A pharmaceutically acceptable salt of tolterodine or hydroxytolterodine according to claim 1 in its crystal form.

6. A pharmaceutical composition comprising a therapeutically effective amount of a salt according to claim 1, and a pharmaceutical diluent or carrier therefor.

7. A pharmaceutical composition according to claim 6, wherein said composition is inhalable or insufflable.

8. A pharmaceutically acceptable salt of tolterodine or hydroxytolterodine, wherein the salt is of an acid selected from the group consisting of $CH_3$—$(CH_2)_{n1}$—COOH, wherein n1 is an integer in the range of 8–12, and HOOC—$(CH_2)_{n2}$—COOH, wherein n2 is an integer in the range of 8–12.

9. A pharmaceutically acceptable salt of tolterodine or hydroxytolterodine according to claim 8 in its crystal form.

10. A pharmaceutical composition comprising a therapeutically effective amount of a salt according to claim 8, and a pharmaceutical diluent or carrier therefor.

11. A pharmaceutical composition according to claim 10, wherein said composition is inhalable or insufflable.

12. A method of treating a disorder selected from the group consisting of asthma, chronic obstructive pulmonary disease (COPD), allergic rhinitis, and urinary disorder, in a mammal, comprising administering to said mammal, in need of such a treatment, a therapeutically effective amount of a pharmaceutically acceptable salt of tolterodine or hydroxytolterodine according to claim 8.

13. A method according to claim 12, wherein the therapeutically effective amount of said salt is administered in a pharmaceutical composition comprising a pharmaceutical diluent or carrier therefor.

14. A method according to claim 13, wherein said administration is performed by inhalation or insufflation.

15. A method according to claim 12 wherein said administration is performed by inhalation or insufflation.

16. A pharmaceutically acceptable salt of tolterodine or hydroxytolterodine, wherein the salt is of an acid selected from the group consisting of naphthoic acid derivatives of from 11 to 27 carbon atoms of the formula:

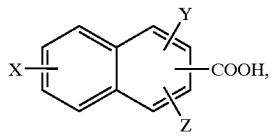

wherein X and Y are independently selected from the group consisting of —H, —OH, —$CH_3$, —F, —Cl, —Br, —I, —COOH, —$NO_2$, —$SO_3H$, and —$CF_3$, and Z is selected from the group consisting of —H and

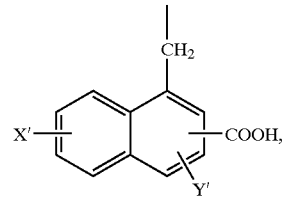

wherein X" and Y" are independently selected from the group consisting of —H, —OH, —$CH_3$, —F, —Cl, —Br, —I, —COOH, —$NO_2$, —$SO_3H$, and —$CF_3$.

17. A pharmaceutically acceptable salt of tolterodine or hydroxytolterodine according to claim 16, wherein X, Y, X", and Y" are independently selected from the group consisting of —H, —OH, and —COOH.

18. A pharmaceutically acceptable salt of tolterodine or hydroxytolterodine according to claim 17, wherein X and X"are —H, and Y and Y"are —OH.

19. A pharmaceutically acceptable salt of tolterodine or hydroxytolterodine according to claim 16 in its crystal form.

20. A pharmaceutical composition comprising a therapeutically effective amount of a salt according to claim 16, and a pharmaceutical diluent or carrier therefor.

21. A pharmaceutical composition according to claim 20, wherein said composition is inhalable or insufflable.

22. A method of treating a disorder selected from the group consisting of asthma, chronic obstructive pulmonary disease (COPD), allergic rhinitis, and urinary disorder, in a mammal, comprising administering to said mammal, in need of such a treatment, a therapeutically effective amount of a pharmaceutically acceptable salt of tolterodine or hydroxytolterodine according to claim 16.

23. A method according to claim 22, wherein the therapeutically effective amount of said salt is administered in a pharmaceutical composition comprising a pharmaceutical diluent or carrier therefor.

24. A method according to claim 23, wherein said administration is performed by inhalation or insufflation.

25. A method according to claim 22, wherein said administration is performed by inhalation or insufflation.

26. A method of treating a disorder elected from the group consisting of asthma, chronic obstructive pulmonary disease (COPD), allergic rhinitis, and urinary disorder, in a mammal, comprising administering to said mammal, in need of such a treatment, a therapeutically effective amount of a pharmaceutically acceptable salt of tolterodine or hydroxytolterodine, wherein the salt is of an acid selected from the group consisting of aliphatic mono- and dicarboxylic acids of from 7 to 24 carbon atoms, alkanedisulfonic acids of from 2 to 4 carbon atoms, naphthoic acid derivatives of from 11 to 27 carbon atoms, maleic acid and fumaric acid.

27. A method according to claim 26, wherein the therapeutically effective amount of said salt is administered in a pharmaceutical composition comprising a pharmaceutical diluent or carrier therefor.

28. A method according to claim 27, wherein said administration is performed by inhalation or insufflation.

29. A method according to claim 26, wherein said administration is performed by inhalation or insufflation.

* * * * *

UNITED STATES PATENT AND TRADEMARK OFFICE
CERTIFICATE OF CORRECTION

PATENT NO. : 7,005,449 B2
APPLICATION NO. : 10/127875
DATED : February 28, 2006
INVENTOR(S) : Michael Hawley et al.

It is certified that error appears in the above-identified patent and that said Letters Patent is hereby corrected as shown below:

Claim 1, column 10, line 67, change "7 to 24 carbon atoms" to --10 to 24 carbon atoms--.

Claim 2, column 11, line 6, change "of 5-16," to --of 8-16,"; line 8, change "of 5-16," to --of 8-16,--.

Claim 3, column 11, line 13, change "of 5-16," to --of 8-16,--; line 15, change "of 5-16." to --of 8-16.--.

Claims 4, column 11, line 17, delete "heptanoic acid,".

Claim 16, column 12, line 15, change "wherein X" and Y" are" to --wherein X' and Y' are--.

Claim 17, column 12, lines 19-20, change "wherein X, Y, X", and Y" are" to --wherein X, Y, X', and Y' are--.

Claim 18, column 12, lines 23-24, change "and X" are" to --and X' are-- and change "and Y" are" to --and Y' are--.

UNITED STATES PATENT AND TRADEMARK OFFICE
CERTIFICATE OF CORRECTION

PATENT NO.        : 7,005,449 B2
APPLICATION NO. : 10/127875
DATED             : February 28, 2006
INVENTOR(S)       : Michael Hawley et al.

It is certified that error appears in the above-identified patent and that said Letters Patent is hereby corrected as shown below:

Claim 26, column 12, line 53, change "7 to 24 carbon atoms," to --10 to 24 carbon atoms--.

Signed and Sealed this

Fourth Day of September, 2007

JON W. DUDAS
*Director of the United States Patent and Trademark Office*